(12) United States Patent
Iemura et al.

(10) Patent No.: US 6,515,158 B2
(45) Date of Patent: Feb. 4, 2003

(54) TONER FOR DEVELOPING ELECTROSTATIC LATENT IMAGE, CHARGE CONTROL AGENT FOR USE IN THE TONER, AND PROCESS FOR PREPARING THE CHARGE CONTROL AGENT

(75) Inventors: Hirofumi Iemura, Tokyo (JP); Koichi Ogawa, Tokyo (JP); Katsuhiko Mizushima, Tokyo (JP)

(73) Assignee: Toyo Ink Manufacturing Co., Ltd., Tokyo (JP)

( * ) Notice: Subject to any disclaimer, the term of this patent is extended or adjusted under 35 U.S.C. 154(b) by 2 days.

(21) Appl. No.: 09/816,401

(22) Filed: Mar. 26, 2001

(65) Prior Publication Data

US 2001/0049068 A1 Dec. 6, 2001

Related U.S. Application Data

(62) Division of application No. 09/267,160, filed on Mar. 12, 1999, now Pat. No. 6,261,731.

(30) Foreign Application Priority Data

Mar. 13, 1998 (JP) .......................... 10-062396

(51) Int. Cl.$^7$ .......................... C07F 11/00; G03G 9/00
(52) U.S. Cl. .................. 556/61; 430/110; 430/106
(58) Field of Search .................. 556/61; 430/110, 430/106

(56) References Cited

U.S. PATENT DOCUMENTS

| | | | | |
|---|---|---|---|---|
| 3,164,620 A | * | 1/1965 | van der Minne et al. | 556/61 |
| 3,887,598 A | * | 6/1975 | Eicke et al. | 556/61 |
| 4,206,064 A | | 6/1980 | Kiuchi et al. | 430/106 |
| 4,762,763 A | | 8/1988 | Nomura et al. | 430/110 |
| 5,045,425 A | | 9/1991 | Swidler | 430/115 |
| 5,393,632 A | | 2/1995 | Ciccarelli et al. | 430/110 |
| 5,976,749 A | | 11/1999 | Sukata et al. | 430/110 |
| 5,994,016 A | | 11/1999 | Kuramoto et al. | 430/110 |

FOREIGN PATENT DOCUMENTS

| | | | | |
|---|---|---|---|---|
| EP | 0 181 081 | | 5/1986 | |
| EP | 0 335 676 | | 10/1989 | |
| EP | 0 488 413 | | 6/1992 | |
| EP | 506 192 | | 9/1992 | |
| EP | 0 761 638 | | 3/1997 | |
| EP | 0 768 576 | | 4/1997 | |
| EP | 0941983 A1 | * | 9/1999 | C07C/51/41 |
| EP | 1225165 A1 | * | 7/2002 | C07C/51/41 |
| GB | 2 090 008 | | 6/1982 | |
| GB | 2 101 757 | | 1/1983 | |
| JP | 63-250662 | | 10/1988 | |
| JP | 2-166462 | | 6/1990 | |
| JP | 2885238 | | 6/1990 | |
| JP | 9-34177 | | 2/1997 | |

OTHER PUBLICATIONS

"Chemical Abstracts", vol. 70, No. 4, (Jan. 27, 1969) Columbus, Ohio, US; abstract No. 13103f, p. 106; col. 2; XP002200043.

"Chemical Abstracts", vol. 70, No. 17, (Apr. 28, 1969) Columbus, Ohio, US; abstract No. 77519d, Fedorova, R. I. et al: "Synthesis and testing of chromium chelates based on dialkyl–substituted salicylic acids" col. 2: XP00220044.

"Chemical Abstracts", vol. 115, No. 22, (Dec. 2, 1991) Columbus, Ohio, US; abstract No. 233658, Zhang, Baolong et al: "Catalytic reactivity and curing course of epoxy resin E–51/MTHPA catalyzed" col. 1; XP002200045.

Diamond, Arthur S. (ed.) Handbook of Imaging Materials, New York: Marcel–Dekker, Inc. pp. 159–171, 178–191, 227–235.

"Paramagnetic Resonance Absorption of Microwaves", by Lancaster et al., Journal of Chemical Physics, vol. 19, No. 9 (Sep. 1951), pp. 1181–1191.

\* cited by examiner

Primary Examiner—Porfirio Nazario-Gonzalez
(74) Attorney, Agent, or Firm—McDermott, Will & Emery

(57) ABSTRACT

A toner for developing an electrostatic latent image is disclosed, which contains as a charge control agent a trivalent chromium salt of salicylic acid or a derivative thereof represented by the general formula:

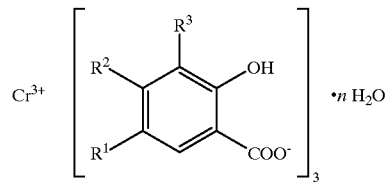

wherein $R^1$, $R^2$ and $R^3$ each represents a hydrogen atom, a saturated or unsaturated, straight or branched alkyl group or, when taken together. $R^1$ and $R^2$ or $R^2$ and $R^3$ form a fused ring optionally having a saturated or unsaturated, straight or branched alkyl group, and n represents 0, 1 or 2. The trivalent chromium salts are formed by adding an aqueous solution of alkali metal salt of salicylic acid or a derivative thereof having a pH of 6.5 to less than 7.0 to an aqueous solution of a chromium (III) halide having a pH of 3.0 to 5.8.

3 Claims, 6 Drawing Sheets

TONER FOR DEVELOPING ELECTROSTATIC LATENT IMAGE, CHARGE CONTROL AGENT FOR USE IN THE TONER, AND PROCESS FOR PREPARING THE CHARGE CONTROL AGENT

This application is a Divisional of Application Ser. No. 09/267,160 filed Mar. 12, 1999 now U.S. Pat. No. 6,261,731.

BACKGROUND OF THE INVENTION (a) Technical Field of Invention

This invention relates to a toner for developing an electrostatic latent image formed by electrophotography, electrostatic recording process, or the like, to a charge control agent for use in producing the toner, and to a process for preparing the charge control agent.

(b) Background of the Art

As a process for developing an electrostatic latent image formed on an electrostatic image carrier such as an electrophotographic light sensitive member or an electrostatic recording medium, there have been known a wet type developing process of using a liquid developer containing a fine toner dispersed in an electrically insulating liquid and a dry type developing process of using a toner containing a colorant, a magnetic particle, etc. dispersed in a binder resin. The dry type developing process includes a process of using a two-component type developer composed of a carrier and a toner, and a process of using a one-component type developer composed of a toner alone (usually a magnetic toner).

These toners for developing an electrostatic latent image contain a colorant such as a dye or a pigment with binder resin and, with magnetic toners, further magnetic particles etc. Usually, however, these components fail to impart desirable charging properties. Therefore, a charge control agent has been used in the toners. As typical examples of conventionally used charge control agents capable of imparting positive charge to toner particles, there are illustrated electron donative materials such as basic dyes (e.g., Nigrosine dyes, triarylmethane dyes, etc.) and quaternary ammonium salts and, as typical examples of those capable of imparting negative charge to toner particles, there are illustrated metal-containing dyes such as metal complexes of monoazo dyes, chromium-containing organic dyes (e.g., Copper Phthalocyanine Green, chromium-containing monoazo dyes, etc.). However, many of these conventional charge control agents have such problem as that they fail to impart good charge control properties to toner particles over a long period of time due to their insufficient dispersibility in toner particles owing to their poor compatibility or wetting properties with a binder resin, or due to their poor stability or some sublimation properties. Further, some conventional charge control agents are colored and are not suited for color toners.

(c) The Prior Art

As charge control agents capable of solving these problems, there have been proposed metal complexes of salicylic acid and derivatives thereof (e.g., Japanese Examined Patent Publication No. S55-42752, Japanese Unexamined Patent Publication Nos. H7-84412 and H9-34177, etc.) and divalent metal salts of salicylic acid and derivatives thereof (e.g., Japanese Examined Patent Publication No. H7-62766, etc.). Many of these charge control agents are only slightly colored and can be advantageously used in color toners. However, further study is required as to uniform dispersibility in resin and charge control properties.

As has been described above, charge control agents to be used in toner particles for developing an electrostatic latent image are required to have good compatibility or wettability with toner binder resins, good stability, and no colors as well as charge control ability. In addition, they are required to provide toner particles having good storage stability, enough durability to be repeatedly used many times and not to exert adverse influences on fixing property or anti-offset property.

SUMMARY OF THE INVENTION

It is, therefore, an object of the invention to provide a toner for developing an electrostatic latent image, which can solve the above-described problems and show excellent properties, a charge control agent having excellent properties, and a process for preparing the charge control agent.

Other objects, features and advantages of the present invention will become apparent from the detailed description of the preferred embodiments of the invention to follow.

As a result of intensive investigations, the inventors have found that trivalent chromium salts of salicylic acid or its derivative produced under specific conditions can satisfy the above-described requirements, thus having completed the present invention based on the finding.

That is, according to the present invention, there is provided a process for preparing a trivalent chromium salt of salicylic acid or its derivative, which comprises adding an aqueous solution of an alkali metal salt of salicylic acid or its derivative of 6.5 to less than 7.0 in pH to an aqueous solution of chromium(III) halide of 3.0 to 5.8 in pH.

Further, according to the present invention, there is provided a charge control agent to be used in a toner for developing an electrostatic latent image, which comprises a trivalent chromium salt of salicylic acid or its derivative prepared by adding an aqueous solution of an alkali metal salt of salicylic acid or its derivative of 6.5 to less than 7.0 in pH to an aqueous solution of chromium(III) halide of 3.0 to 5.8 in pH.

Further, according to the present invention, there is provided a toner for developing an electrostatic latent image, which contains a trivalent chromium salt of salicylic acid or its derivative prepared by adding an aqueous solution of an alkali metal salt of salicylic acid or its derivative of 6.5 to less than 7.0 in pH to an aqueous solution of chromium(III) halide of 3.0 to 5.8 in pH.

DETAILED DESCRIPTION AND PREFERRED EMBODIMENT OF THE INVENTION

Figure 1:
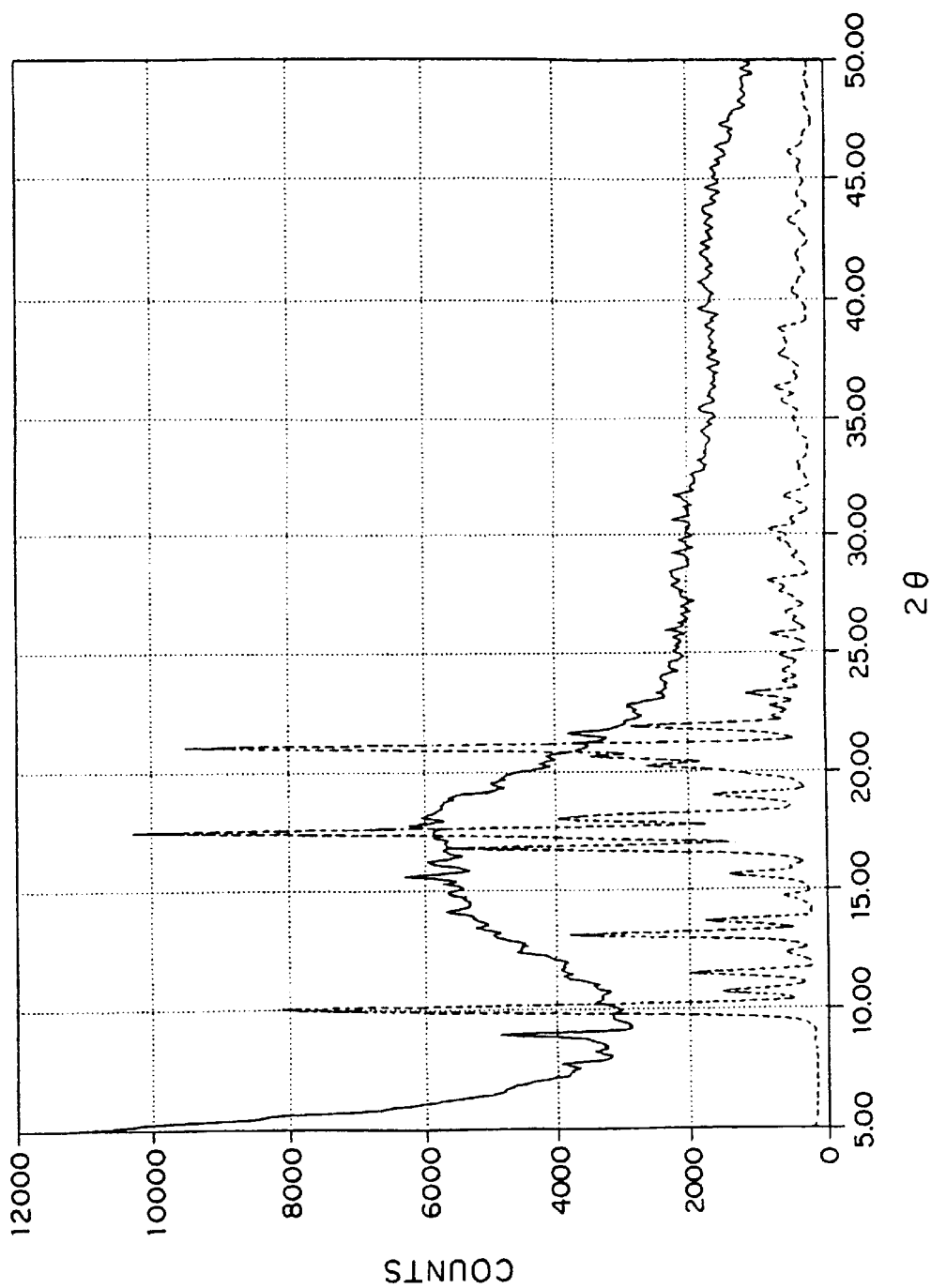
FIG. 1 is a graph showing an X-ray diffraction pattern at an ordinary temperature of the starting material, 3,5-di-tert-butylsalicylic acid and that of trivalent chromium salt of 3,5-di-tert-butylsalicylic acid prepared according to the present invention.

As has been described herein before, trivalent chromium salts of salicylic acid or its derivative of the present invention useful as charge control agents are prepared by adding an aqueous solution of an alkali metal salt of salicylic acid or its derivative of 6.5 to less than 7.0 in pH to an aqueous solution of a chromium(III) halide of 3.0 to 5.8 in pH.

A preferred salicylic acid or its derivative used in the above-described process is a compound represented by the following general formula 1;

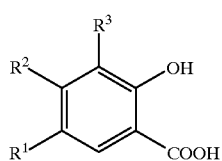

(1)

wherein
$R^1$, $R^2$ and $R^3$ each represents a hydrogen atom, a saturated or unsaturated, straight or branched alkyl group or, when taken together, $R^1$ and $R^2$ or $R^2$ and $R^3$ form a fused ring optionally having a saturated or unsaturated, straight or branched alkyl group.

The trivalent chromium salt of salicylic acid or its derivative prepared according to the above-described process of the present invention by using salicylic acid or its derivative represented by general formula 1 is represented by the following general formula 2;

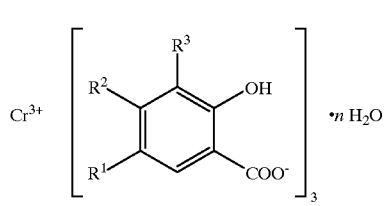

(2)

wherein
$R^1$, $R^2$ and $R^3$ each represents a hydrogen atom, a saturated or unsaturated, straight or branched alkyl group or, when taken together, $R^1$ and $R^2$ or $R^2$ and $R^3$ form a fused ring optionally having a saturated or unsaturated, straight or branched alkyl group, and n represents 0, 1 or 2.

As to pH value of the aqueous solution of chromium(III) halide to be used in the above-described process of the present invention, a preferred range varies depending upon whether $R^1$ and $R^2$ or $R^2$ and $R^3$ of salicylic acid or its derivative form a fused ring or not. That is, where $R^1$ and $R^2$ or $R^2$ and $R^3$ of salicylic acid or its derivative do not form a fused ring, pH of the aqueous solution of chromium(III) halide is preferably 3.8 to 4.1, more preferably 3.9 to 4.02 and, where $R^1$ and $R^2$ or $R^2$ and $R^3$ of salicylic acid or its derivative form a fused ring, pH of the aqueous solution of chromium(III) halide is preferably 4.5 to 5.8, more preferably 5.0 to 5.5. If pH of the aqueous solution of chromium (III) halide is outside the scope of 3.0 to 5.8, it becomes difficult to form intended trivalent chromium salt of salicylic acid or its derivative or, if formed, with a decreased yield, thus being practically problematical.

The above-described aqueous solution of chromium(III) halide of 3.0 to 5.8 in pH is prepared by gradually adding an aqueous solution of alkali metal hydroxide to an aqueous solution of chromium(III) halide (pH 1.9–2.3) spending enough time. As the aqueous solution of alkali metal hydroxide, an aqueous solution of NaOH of usually about 0.5 to about 2% (by weight, and "%" represent '% by weight' hereinafter) in concentration, for example, about 1% is used and, as the aqueous solution of chromium(III) halide, an aqueous solution of chromium(III) halide of usually about 5 to about 20%, for example, about 10% is used. If concentration of the aqueous solution of the alkali metal hydroxide is less than 0.5%, it will take a prolonged period of time to adjust pH, while if more than 2%, chromium hydroxide is liable to be formed. The thus prepared aqueous solution of chromium(III) halide (pH 3.0 to 5.8) is desirably introduced directly without allowing to stand to the next step, because the aqueous solution would suffer reduction in pH upon being allowed to stand.

On the other hand, the aqueous solution of alkali metal salt of salicylic acid or its derivative to be used for the reaction has a pH of 6.5 to less than 7.0, preferably 6.7 to 6.9. This aqueous solution of alkali metal salt of salicylic acid or its derivative is usually prepared by adding salicylic acid or its derivative in an about equal molar amount based on alkali metal to an alkali metal aqueous solution of about 0.5 to about 5%, for example, 1 to 2% in concentration heated to usually 50 to 70° C., preferably about 60° C. to about 65° C., and stirring this aqueous solution with keeping its temperature at this level to thereby dissolve salicylic acid or its derivative. If pH of the aqueous solution of the alkali metal salt of salicylic acid or its derivative is less than 6.5, there results much insoluble matters in the formed solution whereas, if 7.0 or more in pH, there is formed $Cr(OH)_3$, thus not being favorable. If the pH of said aqueous solution is within the range of from 6.7 to 6.9, the salicylic acid or its derivative represented by the foregoing general formula 2 can be obtained in a high yield, thus pH of the aqueous solution being preferably 6.7 to 6.9. Temperature for preparing the aqueous solution of the alkali metal salt of salicylic acid or its derivative is to be decided taking solubility of the alkali metal salt of salicylic acid or its derivative into consideration, and hence the temperature of the above-described range is usually employed.

Further, upon adding the aqueous solution of alkali metal salt of salicylic acid or its derivative having a pH of 6.5 to less than 7.0 to the aqueous solution of chromium(III) halide of 3.0 to 5.8 in pH, it is preferred to gradually add with spending enough period of time, since rapid addition of the aqueous solution of alkali metal salt would decrease the yield. Chromium(III) halide is usually used in an amount of 1 mol or more based on 3 mols of salicylic acid or its derivative, preferably more than 1 mol. After completion of the dropwise addition of the aqueous solution of the alkali metal salt of salicylic acid or its derivative, stirring is continued for an enough period of time, for example, about one hour, to complete the reaction. Then, the reaction mixture is filtered to collect the reaction product, followed by washing, drying and pulverizing the product to obtain the end product containing the compound represented by the general formula 2 useful as a charge control agent. In this occasion, temperature of the aqueous solution of chromium (III) halide of 3.0 to 5.8 in pH, temperature of the aqueous solution of alkali metal salt of salicylic acid or its derivative, temperature of the mixture of these solutions, and temperature upon suction filtration are usually kept in the range of from about 50 to about 70° C., preferably 60 to 65° C. Filtration can be conducted in a conventionally known manner such as suction filtration, centrifugation or the like. As the salicylic acid derivatives to be used in the present invention, those represented by the foregoing general formula 1 are preferred. Preferred examples of the substituents $R^1$, $R^2$ and $R^3$ in the general formula 1 include a straight or branched alkyl group containing 1 to 12 carbon atoms such as a methyl group, an ethyl group, a propyl group, an isopropyl group, a butyl group, an isobutyl group, a sec-butyl group, a tert-butyl group, an amyl group, an isoamyl group, an octyl group, a tert-octyl group, a dodecyl group, etc. and an unsaturated alkyl group such as an allyl group, a propenyl group, a butenyl group, etc. Of these, saturated or unsaturated, straight or branched alkyl groups containing 1 to 8 carbon atoms are more preferred, with a tert-butyl group and a tert-octyl group being particularly preferred. When $R^1$ and $R^2$ or $R^2$ and $R^3$ are taken together to form a fused ring optionally having a saturated or unsaturated, straight or branched alkyl group, they preferably form a benzene ring, thus the salicylic acid or its derivative being a hydroxynaphthoic acid type compound. Particularly preferred specific examples of the salicylic acid or its derivative include 3,5-di-tert-butylsalicylic acid and 3-hydroxy-2-naphthoic acid.

The toner of the present invention for developing an electrostatic latent image contains, as a charge control agent, trivalent chromium salt of salicylic acid or its derivative prepared according to the above-described process of the present invention. The charge control agent contains at least trivalent chromium salt of salicylic acid or its derivative represented by the foregoing general formula 2. As to the charge control agent, it suffices to use it in an amount necessary to impart desired charge to the toner. For example, the charge control agent is preferably added in an amount of about 0.05 to about 10 parts by weight per 100 parts by weight of resin.

As constituents of the toner of the present invention for developing an electrostatic latent image, known materials for constituting toner such as binder resins, colorants or powder of magnetic material, and if necessary, releasing agents, lubricants, flowability-improving agents, abrasives, conductivity-imparting agents, image delamination-preventing agents, etc. may be used in addition to the charge control agent of the present invention. Additionally, there may be used other known negatively chargeable charge control agents such as azo dyes containing a metal (e.g., Cr, Co, Al or Fe), charge control agent which is resin type (CCR), etc. in addition to the charge control agent of the present invention. The amount of such other charge control agents are not particularly limited as long as the effect of the charge control agent of the present invention is attained.

As a binder resin to be used for the toner of the present invention for developing an electrostatic latent image, any of known one may be used that is conventionally known as a binder resin for toners for developing an electrostatic latent image. The usable binder resin is exemplified by homopolymers of styrene or its derivative such as polystyrene, poly-p-chlorostyrene, polyvinyltoluene, etc.; styrene copolymers such as a styrene-p-chlorostyrene copolymer, a styrene-vinyltoluene copolymer, a styrene-vinylnaphthalene copolymer, a styrene-acrylate copolymer, a styrene-methacrylate copolymer, a styrene-methyl α-chloromethacrylate copolymer, a styrene-acrylonitrile copolymer, a styrene-vinyl methyl ether copolymer, a styrene-vinyl ethyl ether copolymer, a styrene-vinyl methyl ketone copolymer, a styrene-butadiene copolymer, a styrene-isoprene copolymer, a styrene-acrylonitrile-indene copolymer, etc.; polyvinyl chloride; phenol resin; natural resin-modified phenol resin; natural resin-modified maleic acid resin; acrylic resin; methacrylic resin; polyvinyl acetate; silicone resin; polyester resin; polyurethane; polyamide resin; furan resin; epoxy resin; xylene resin; polyvinyl butyral; terpene resin; cumarone-indene resin; petroleum resin; etc.

In addition, cross-linked styrene copolymers are also preferred binder resins. As the comonomer for styrene monomer of the styrene copolymers, there may be used one or more of monocarboxylic acids having a double bond or derivatives thereof such as acrylic acid, methyl acrylate, ethyl acrylate, butyl acrylate, dodecyl acrylate, octyl acrylate, 2-ethylhexyl acrylate, phenyl acrylate, methacrylic acid, methyl methacrylate, ethyl methacrylate, butyl methacrylate, octyl methacrylate, acrylonitrile, methacrylonitrile, acrylamide, etc.; dicarboxylic acids having a double bond or derivatives thereof such as maleic acid, methyl maleate, butyl maleate, dimethyl maleate, etc.; vinyl esters such as vinyl chloride, vinyl acetate, vinyl benzoate, etc.; ethylenic olefins such as ethylene, propylene, butylene, etc.; vinyl ketones such as vinyl methyl ketone, vinyl hexyl ketone, etc.; vinyl ethers such as vinyl methyl ether, vinyl ethyl ether, vinyl isobutyl ether, etc.; and the like.

As the cross linking agents; those compounds which have two or more polymerizable double bonds are mainly used. For example, aromatic divinyl compounds such as divinylbenzene, divinylnaphthalene, etc.; carboxylic esters having two double bonds such as ethylene glycol diacrylate, ethylene glycol dimethacrylate, 1,3-butanediol dimethacrylate, etc.; divinyl compounds such as divinylaniline, divinyl ether, divinyl sulfide, divinyl sulfone, etc.; and compounds having three or more vinyl groups may be used alone or in combination. Particularly, styrene copolymers having a molecular weight distribution measured according to GPC wherein at least one peak exists in the region of from $3 \times 10^3$ to $5 \times 10^4$ and at least one peak or a shoulder exists in the region of from $10^5$ above are preferred in view of fixing properties.

Molecular weight distribution is measured according to GPC under the following conditions: A column is stabilized in a 40° C. heat chamber, and about 100 $\mu$l of a test sample solution in tetrahydrofuran (THF) is injected into the column at the temperature while introducing there into THF as a solvent at a flow rate of 1 ml/min to measure. Upon measurement of the molecular weight of the sample, molecular weight distribution of the sample was calculated based on the relation between the logarithmic value of calibration curve prepared from several monodisperse polystyrene standard samples and the count number. As the standard polystyrene samples for preparing the calibration curve, those which have a molecular weight of about $10^2$ to about $10^7$ manufactured by, for example, TOSO K.K. or SHOWA DENKO K.K. are used, with at least about 10 points being preferably plotted. As a detector, an RI (Refraction Index) detector is used. Additionally, as the column, a plurality of commercially available polystyrene gel column are preferably used. For example, a combination of Shodex GPC KF-801, 802, 803, 804, 805, 806, 807 and 800P manufactured by SHOWA DENKO K.K. or a combination of TSK gel G1000H($H_{XL}$), G2000H($H_{XL}$), G3000H ($H_{XL}$), G4000H($H_{XL}$), G5000H($H_{XL}$), G6000H($H_{XL}$), G7000H($H_{XL}$), TSK guard column manufactured by TOSO K.K. may be used.

Test samples are prepared in the following manner. A sample is placed in THF and, after allowing to stand for several hours, the mixture is sufficiently shook till no insoluble matters of the sample exist, followed by allowing the mixture to stand for 12 hours or longer. In this occasion, the sample is to be allowed to stand in THF for 24 hours or longer in total. Then, the mixture is passed through a sample-processing filter (pore size: 0.45 to 0.5 µm; e.g., MAI SHORI DISC H-25-5 made by TOSO K.K. or EKIKURO DISC 25CR made by German Science Japan K.K.) to prepare a sample for GPC. Sample concentration is adjusted so that the resin component is contained in a concentration of 0.5 to 5 mg/ml.

Additionally, a polymerization initiator is used upon production of the vinyl polymer. As the polymerization initiator, any of conventionally known ones may be used. For example, benzoyl peroxide, lauroyl peroxide, tert-butyl hydroperoxide, tert-butyl peroxybenzoate, di-tert-butyl peroxide, cumene hydroperoxide, dicumyl peroxide, azoisobutylonitrile, azobisvaleronitrile, etc. may favorably be used. These initiators are used generally in an amount of 0.2 to 5% by weight based on vinyl monomer. Polymerization temperature is properly selected depending upon kinds of a monomer and an initiator to be used.

Polyester resins are also preferred as binder resins for the toner of the present invention for developing an electrostatic latent image. As the alcohol component constituting such polyester resins, there are illustrated diols such as ethylene glycol, propylene glycol, 1,3-butanediol, 1,4-butanediol, 2,3-butanediol, diethylene glycol, triethylene glycol, 1,5-pentanediol, 1,6-hexanediol, neopentyl glycol, 2-ethyl-1,3-hexanediol, hydrogenated bisphenol A, bisphenol derivatives represented by the following general formula 3 etc.; and polyhydric alcohols such as glycerin, sorbitol, sorbitan, etc.

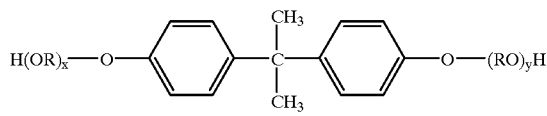

(3)

wherein
R represents an ethylene or propylene group, x and y each represents an integer of 1 or more, provided that the average of x+y is 2 to 10.

As the acid component, there are illustrated dicarboxylic acids such as benzenedicarboxylic acids or the anhydrides thereof (e.g., phthalic acid, terephthalic acid, isophthalic acid, phthalic anhydride, etc.), alkyldicarboxylic acids or the anhydrides thereof (e.g., succinic acid, adipic acid, sebacic acid, azelaic acid, etc.), succinic acid substituted by an alkyl group containing 16 to 18 carbon atoms or the anhydrides thereof, unsaturated dicarboxylic acids or the anhydrides thereof (e.g., fumaric acid, maleic acid, citraconic acid, itaconic acid, etc.); and carboxylic acids having 3 or more carboxyl groups (e.g., trimellitic acid, pyromellitic acid, benzophenonetetracarboxylic acid, and the anhydrides thereof, etc.).

Preferred alcohol components are those bisphenol derivatives which are represented by the foregoing general formula 3, and preferred acid components are dicarboxylic acids such as phthalic acid, terephthalic acid, isophtalic acid, or its anhydride, succinic acid, n-dodecenylsuccinic acid or its anhydride, fumaric acid, maleic acid, maleic anhydride, etc.; and tricarboxylic acids such as trimellitic acid or its anhydride.

The above-described polyester resins preferably have an acid value of 40 mg KOH/g or less as a toner. If the acid value is 40 mg KOH/g or less, serious deterioration of abrasion charging property can be prevented even when left in a high-humidity environment for a long period of time, thus such acid value being preferred. More preferably, the acid value be 30 mg KOH/g or less, since abrasion charging property is stabilized even when the number of copies increases. In particular, polyester resins having the toner acid value of from 1 to 20 mg KOH/g are preferred, since no deterioration of frictional electrification property takes place even after being left in a high-humidity environment for a long period of time, and the toner acquires completely the same electrified quantity as before being left upon being shook with a carrier, with the charging rate being rapid and no gradual increase in electrified quantity taking place as the number of copies increases.

Additionally, in the present invention, measurement of acid value may be conducted by applying the method of JIS K-0070. The acid value is represented in terms of the amount of potassium hydroxide in mg necessary for neutralizing 1 g of the toner. With toners containing a magnetic material, however, the magnetic material is previously dissolved away with an acid, and 1 g of the residue is used as the sample to be neutralized.

In the case of employing a pressure-fixing process, binder resins for pressure-fixable toners may be used. For example, there are illustrated polyethylene, polypropylene, polymethylene, polyurethane elastomer, ethylene-ethyl acrylate copolymers, ethylene-vinyl acetate copolymers, ionomer resins, styrene-butadiene copolymers, styrene-isoprene copolymers, linear saturated polyesters, paraffins, etc.

As colorants for the toner of the present invention for developing an electrostatic latent image, any of those which have conventionally been used in production of toners may be used. Examples of such colorants include metal salts of fatty acids, various types of carbon black, and dyes and pigments of phthalocyanine, Rhodamine, quinacridone, triarylmethane, anthraquinone, azo, diazo, etc. These may be used alone or as a mixture of two or more of them.

The toner of the present invention for developing an electrostatic latent image may contain a powder of magnetic material. Usable magnetic materials may be any of those alloys, compounds, etc. which contain a ferromagnetic element and have conventionally been used in producing magnetic toners. Examples of such magnetic materials include iron oxides or compounds of a divalent metal and iron oxide such as magnetite, maghetite, ferrite, etc., metals such as iron, cobalt, nickel, etc., alloys thereof with a metal such as aluminum, cobalt, copper, lead, magnesium, tin, zinc, antimony, beryllium, bismuth, cadmium, calcium, manganese, selenium, titanium, tungsten, vanadium, etc., and a mixture thereof. These magnetic materials have an average particle size of preferably about 0.1 to about 2 µm, and more preferably about 0.1 to about 0.5 µm. The magnetic material may be contained in the toner in an amount of from about 20 to about 200 parts by weight, preferably 40 to 150 parts by weight, based on 100 parts by weight of the thermoplastic resin. The toner preferably has a saturation magnetization of 15 to 35 emu/g (measured in a magnetic field of 10 kOe).

The toner of the present invention may be mixed with a carrier to use as a two-component toner. As the carrier to be used together with the toner of the present invention, any of conventionally known carriers may be used. As carriers to be used, there are illustrated, for example, a magnetic powder such as an iron powder, a ferrite powder, a nickel powder, etc., glass beads, and a magnetic powder or beads surface-treated with a resin or the like. Resins for treating (coating) the surface of carrier particles include a styrene-acrylic ester copolymer, a styrene-methacrylic ester copolymer, an acrylic ester copolymer, a methacrylic ester copolymer, a fluorine-containing resin, a silicon-containing resin, a polyamide resin, an ionomer resin, a polyphenylene sulfide resin, etc. or a mixture thereof. Of these, fluorine-containing resins and silicon-containing resins are particularly preferred since they form a less amount of spent toner.

The toner of the present invention containing the charge control agent preferably has a weight average particle size of 3 to 15 $\mu$m. More preferably, the toner has a particle size distribution wherein toner particles having a particle size of 5 $\mu$m or less account for 12 to 60% by number of particles, toner particles having a particle size of 8 to 12.7$\mu$m account for 1 to 33% by number of particles, and toner particles having a particle size of 16 $\mu$m or more account for 2.0% by weight of particles or less and has a weight average particle size of 4 to 10 $\mu$m in view of developing properties. Additionally, particle size distribution of the toner can be measured by, for example, Coalter-Counter method.

The toner of the present invention may further contain, if necessary, known additives having been used in production of toners such as a releasing agent, a lubricant, a flowability-improving agent, an abrasive, a conductivity-imparting agent, a image delamination-preventing agent, etc. which may be used internally or externally. Examples of the releasing agent include, for example, wax-like substances such as low molecular weight polyethylene, low molecular weight polypropylene, microcrystalline wax, carnauba wax, sazol wax, paraffin wax, etc. These may be added to the toner in an amount of usually from about 0.5 to about 5% by weight. Examples of the lubricant include polyvinylidene fluoride, zinc stearate, etc., examples of the flowability-improving agent include colloidal silica, aluminum oxide, titanium oxide, etc., examples of the abrasive include cerium oxide, silicon carbide, strontium titanate, tungsten carbide, calcium carbonate, etc., and examples of the conductivity-imparting agent include carbon black, tin oxide, etc. Fine powders of fluorine-containing polymers such as polyvinylidene fluoride etc. are preferred in view of flowability, abrasive property, charge stability, etc.

The toner of the present invention can be produced according to a conventionally known process for producing toners. Generally, the above-described toner constituents are well mixed in a mixer such as a ball mill, a Henschel mixer, etc., well kneaded using a hot roll kneader, a uniaxial or biaxial extruder or like hot kneader and, after cooling to solidify, mechanically roughly crushed using a crushing machine such as a hammer mill etc., then finely pulverized by a jet mill or the like, followed by classification. However, the process for producing the toner is not limited only to the above-described process, but there may be arbitrarily employed other processes such as a process of dispersing other constituents than a binder resin in the solution of binder resin, and spray-drying the dispersion, a so-called microencapsulation process, a polymerization process of conducting emulsion or suspension polymerization of monomers for preparing the binder resin under the existence of other constituent for toner, etc.

The process of the present invention for preparing the charge control agent, the toner of the present invention for developing an electrostatic latent image, and process for producing the toner are now described in more detail by reference to the following Examples which, however, are construed to be illustrative and not construed to be limitative at all.

EXAMPLE 1

Preparation of chromium(III) 3,5-di-tert-butylsalicylate 450 g of water and 7.2 g of NaOH were placed in a 500-cc beaker, and the mixture was heated under stirring to completely dissolve NaOH. This NaOH aqueous solution was heated to 65° C., and 45 g of 3,5-di-tert-butylsalicylic acid was added thereto under stirring. The mixture was further stirred while keeping the temperature at 65° C. to dissolve 3,5-di-tert-butylsalicylic acid. When pH of the dissolved solution became 6.8, heating and stirring were discontinued, and the solution was filtered to remove insoluble 3,5-di-tert-butylsalicylic acid, thus a brown filtrate being obtained. Separately, 37.2 g of a 40% $CrCl_3$ solution and 120 g of water were placed in a 500-cc beaker to prepare a chromium (III) chloride solution having a pH of 2.1. To this chromium (III) chloride solution was gradually added 120 g of 1% NaOH aqueous solution with spending enough time to obtain a solution of 3.95 in pH. Then, this solution was transferred into a 2-liter beaker, and diluted with water to make the total amount 350 g. This chromium(III) chloride solution was heated to 60° C. and, under stirring, the above-described solution of 3,5-di-tert-butylsalicylic acid kept at 60° C. was dropwise added thereto over a period of time of 1.5 to 2 hours. As the addition proceeded, the reaction solution gradually assumed a light green color. After completion of the dropwise addition, stirring was further continued for 1 hour at a temperature of 60 to 65° C., and the reaction solution was suction filtered and washed with water to obtain 170 g of a reaction product (wet). The pH of the filtrate was 4.00. The reaction product collected by filtration was dried at 50° C. for about 14 hours, and the dried product was pulverized to obtain 70 g of an end product. The reaction product is completely soluble in carbon tetrachloride.

The reaction product was subjected to X-ray diffraction measurement, ESR (Electron Spin Resonance) measurement, IR (Infrared) spectrum measurement, $^{13}$C-NMR (Nuclear Magnetic Resonance) measurement and FD-MS (Mass Spectrum) measurement to obtain the results shown in FIGS. 1 to 6. FIG. 1 shows the X-ray diffraction pattern of the starting material 3,5-di-tert-butylsalicylic acid and that of the reaction product measured at an ordinary temperature. In FIG. 1, solid line corresponds to the reaction product and broken line to 3,5-di-tert-butylsalicylic acid. The results of the measurement reveal that the reaction product does not have a peak derived from the starting material, and does not have such a high crystallinity.

Figure 2:
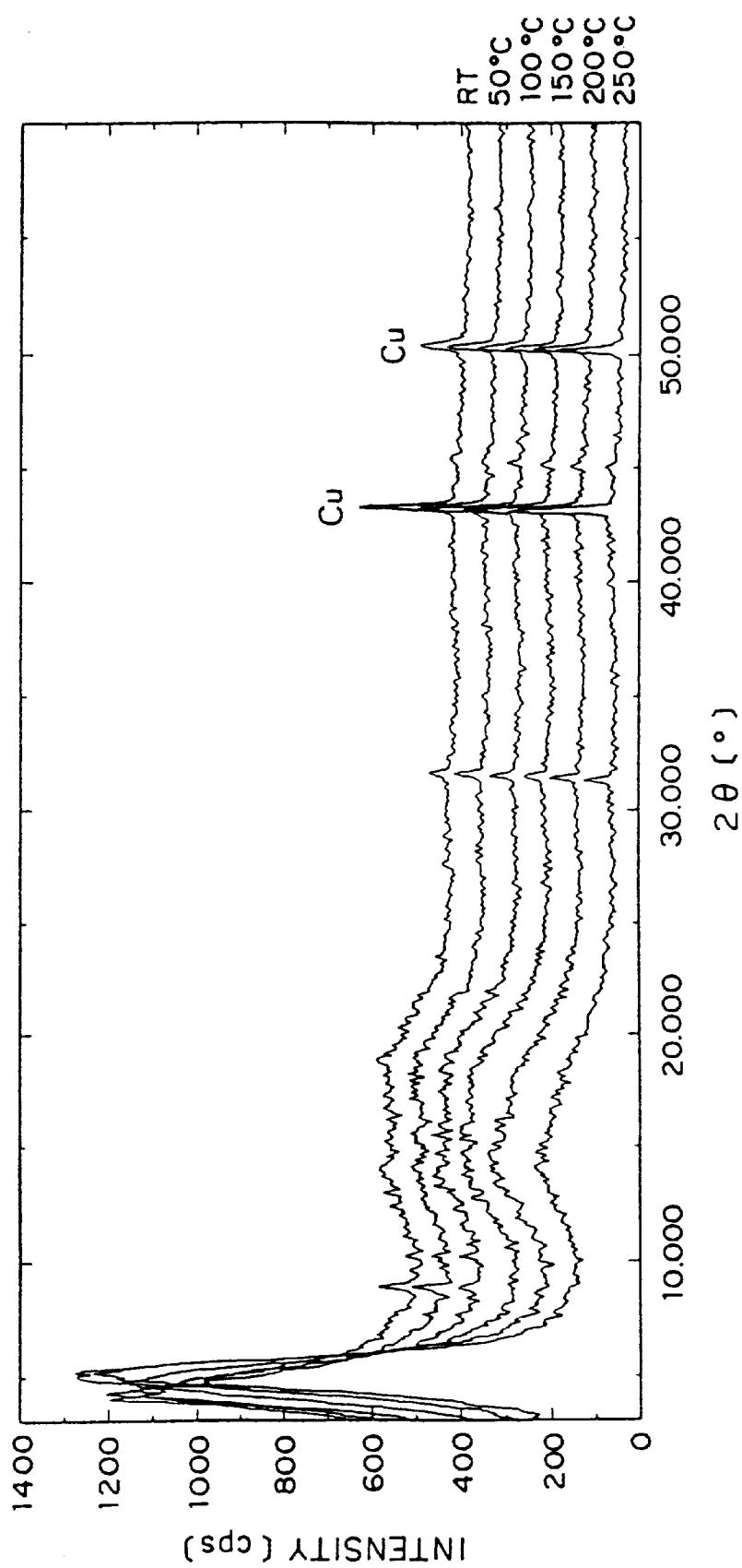
FIG. 2 is a graph showing X-ray diffraction patterns at several elevated temperatures of trivalent chromium salt of 3,5-di-tert-butylsalicylic acid prepared according to the present invention.

FIG. 2 shows an X-ray diffraction pattern of the reaction product measured at an elevated temperature. A peak at 2θ=31.64 becomes clear by heating. This result reveals that the reaction product contains crystal water.

Figure 3:
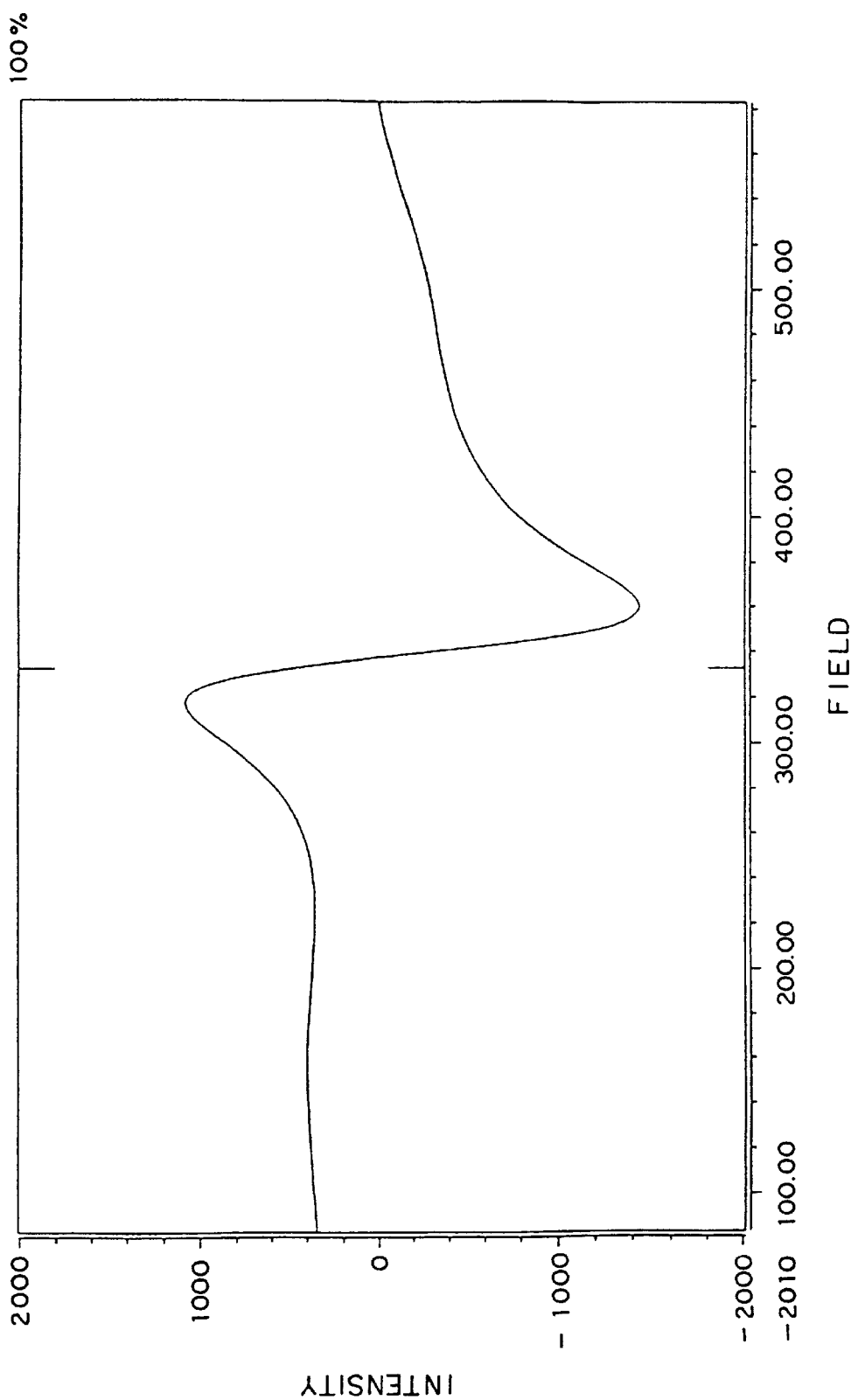
FIG. 3 is a graph showing an ESR (Electron Spin Resonance) spectrum of trivalent chromium salt of 3,5-di-tert-butylsalicylic acid prepared according to the present invention.

FIG. 3 shows results of measurement of ESR of the reaction product. A signal for chromium is detected at g=1.98, and the valence number of Cr metal is three since width of the signal is broad. Divalent chromium does not give any signal, whereas 5-valent chromium gives a sharp signal at g=1.98.

Figure 4:
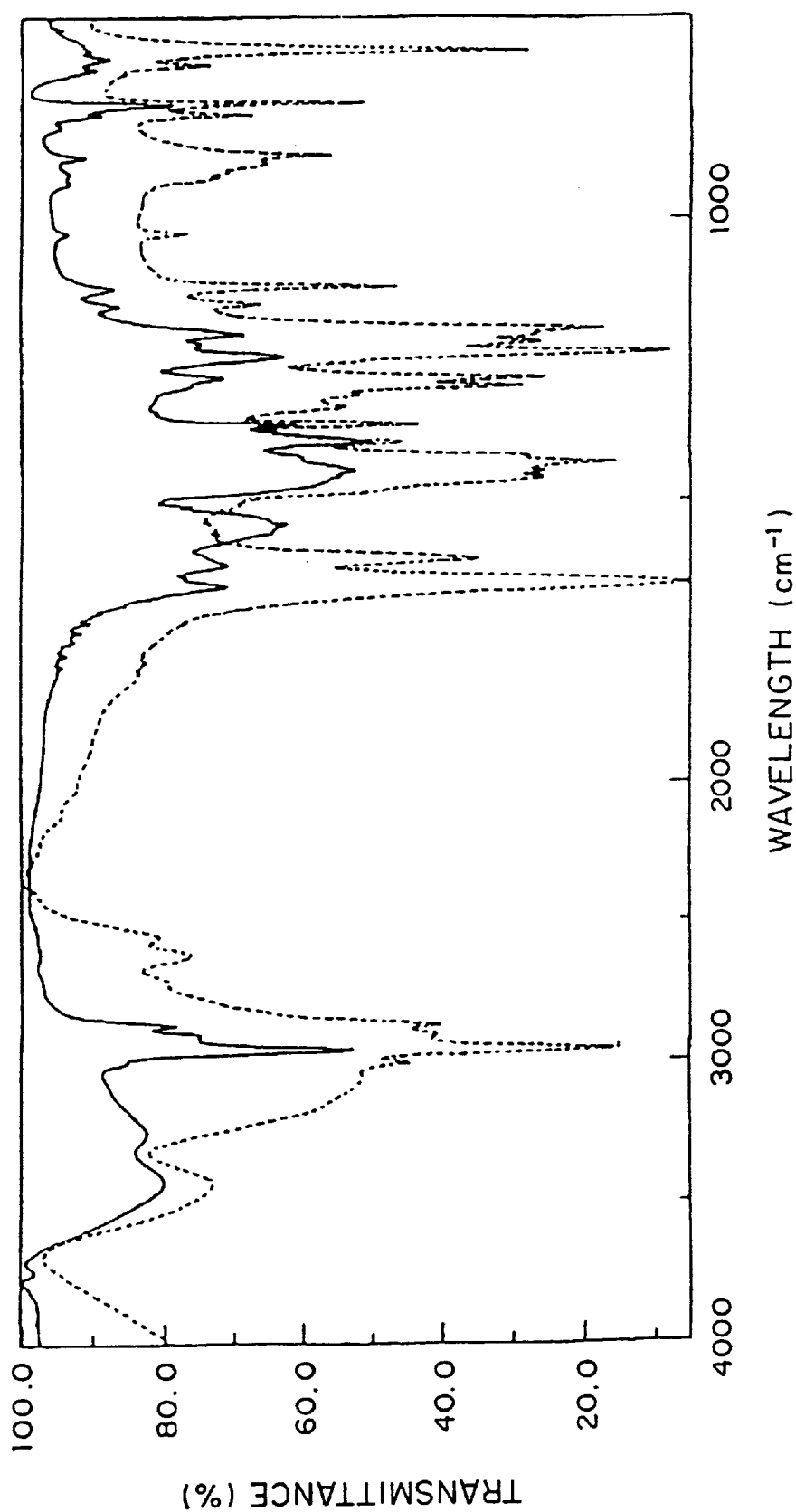
FIG. 4 is a graph showing an infrared absorption spectrum of the starting material, 3,5-di-tert-butylsalicylic acid and that of trivalent chromium salt of 3,5-di-tert-butylsalicylic acid produced according to the present invention.

FIG. 4 shows infrared absorption spectra of the starting material, 3,5-di-tert-butylsalicylic acid and the reaction product. In FIG. 4, solid line shows an infrared absorption spectrum for the reaction product and broken line for 3,5-di-tert-butylsalicylic acid. The reaction product shows a big absorption at 1550 cm$^{-1}$ which is a peak for —COO_ (carboxylate), whereas the starting material, 3,5-di-tert-butylsalicylic acid shows no absorption at 1550 cm$^{-1}$. From these results, it seems that —H of the carboxyl group of 3,5-di-tert-butylsalicylic acid is removed and forms a metal salt (Cr salt).

Figure 5:
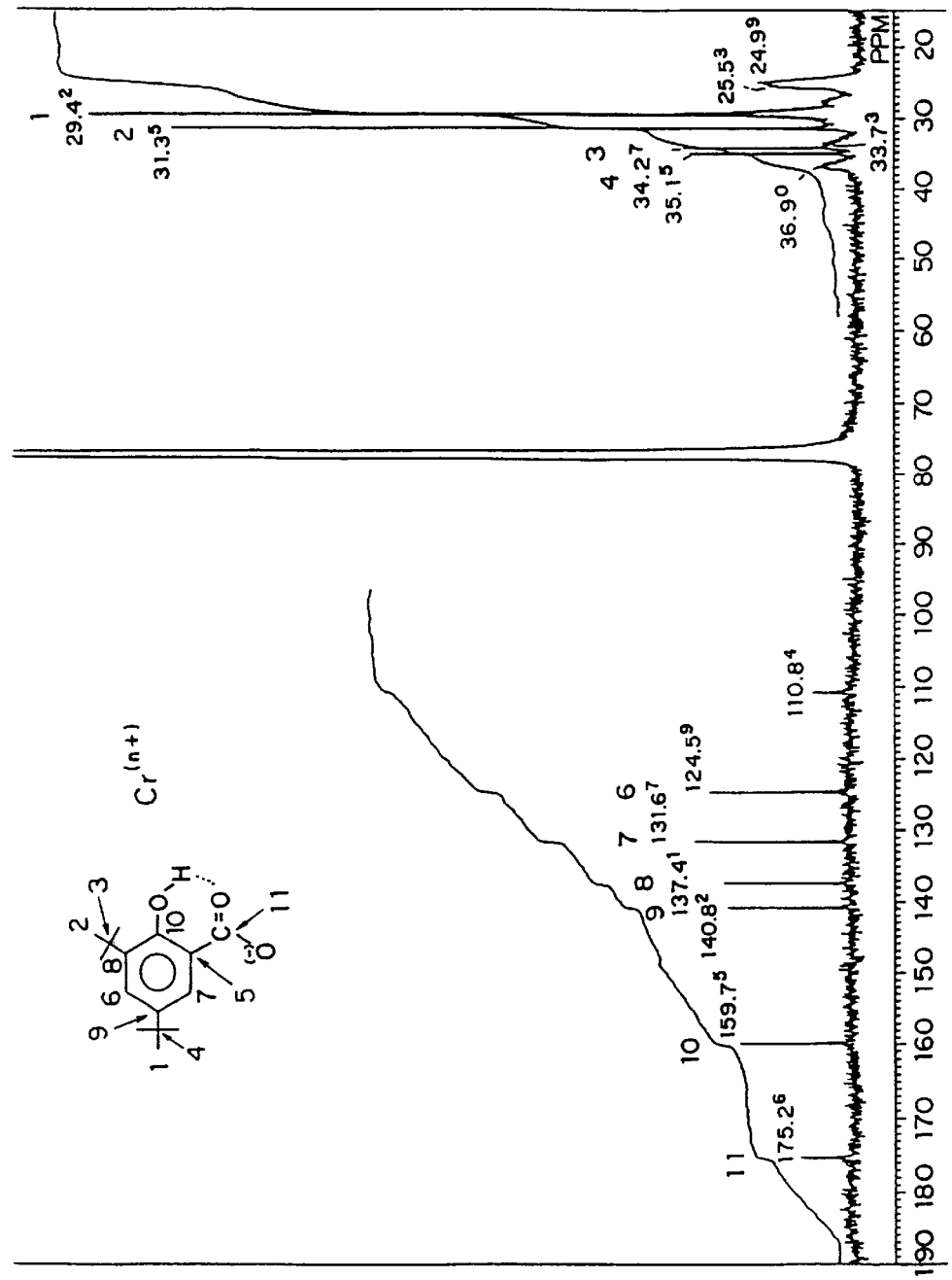
FIG. 5 is a graph showing $^{13}$C-NMR spectrum of trivalent chromium salt of 3,5-di-tert-butylsalicylic acid prepared according to the present invention.

FIG. 5 shows the results of measurement of $^{13}$C-NMR of the reaction product. In FIG. 5, main peaks are assigned. From the results, the reaction product is speculated to be a Cr salt of 3,5-di-tert-butylsalicylic acid.

Figure 6:
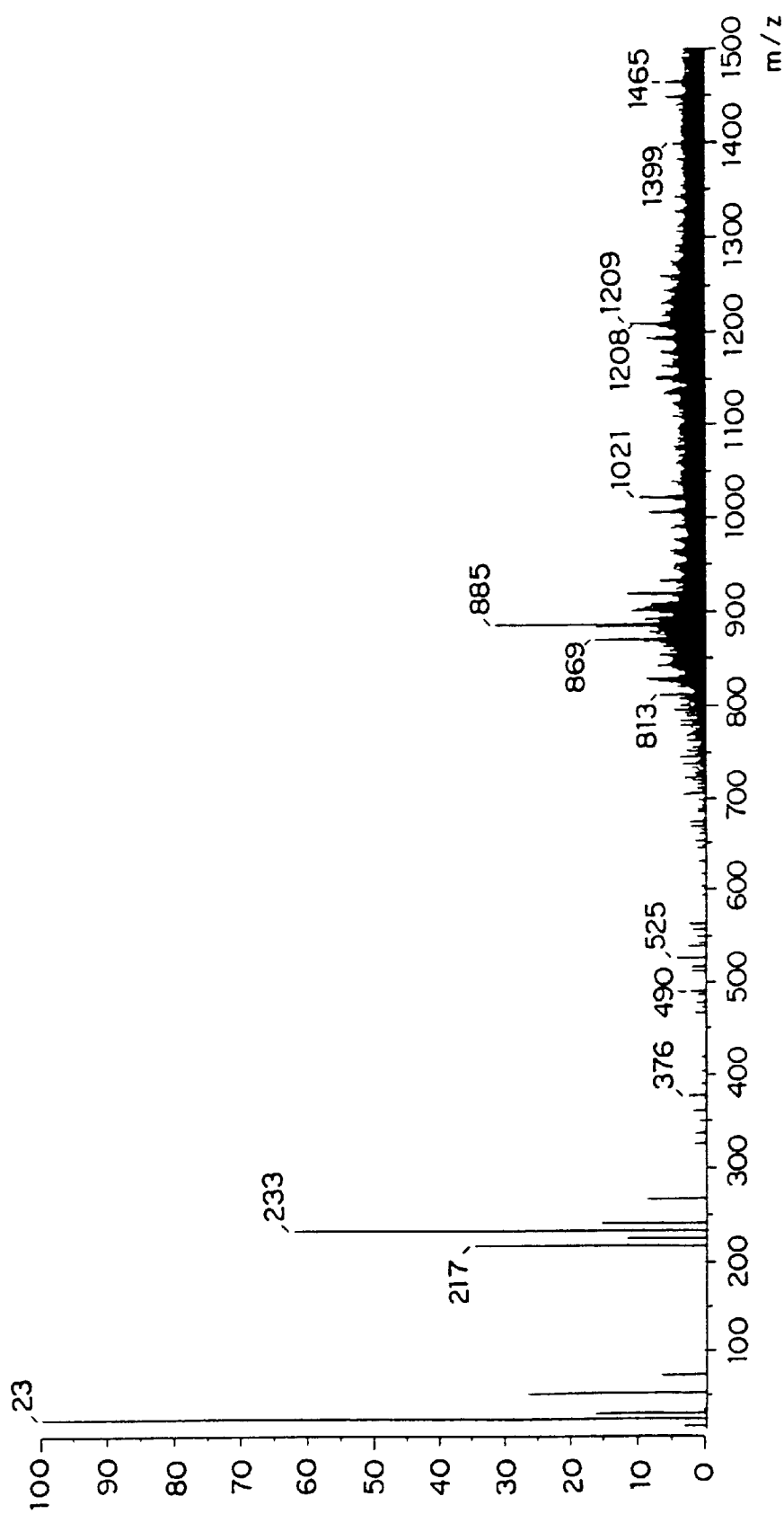
FIG. 6 is a graph showing FD-MS spectrum of trivalent chromium salt of 3,5-di-tert-butylsalicylic acid prepared according to the present invention.

FIG. 6 shows an FD-MS (mass spectrum) of the reaction product. As is clear from FIG. 6, the reaction product is considered to be a mixture. Main compound in the reaction product is a substance having a molecular weight of 885. This is surmised to be a trivalent Cr salt of 3,5-di-tert-butylsalicylic acid monohydrate (molecular weight:863).

Besides, mass spectrometry by ICP-MS gave the result of 76,800 with Cr. This result reveals that the content of Cr (trivalent) of the thus obtained compound is 7.68% by weight but, since theoretical amount (wt %) of Cr in the Cr (trivalent) salt of 3,5-di-tert-butylsalicylic acid monohydrate is 6.03, it seems that the product contains other products than Cr(trivalent) salt of 3,5-di-tert-butylsalicylic acid.

From these analytical results, the reaction product is considered to be a mixture containing as a major component a salt of trivalent Cr with 3 mols of 3,5-di-tert-butylsalicylic acid to which salt one molecule of water is added. A reason for the presence of many co-existing compounds may be that hexa-aqua ion is instantly produced upon dissolution of chromium chloride in water, leading to the following equilibrium state. However, this is merely a speculation of the inventor and does not limit the present invention at all.

EXAMPLE 2

| | |
|---|---|
| Styrene-n-butyl methacrylate copolymer | 93 parts by weight |
| Phthalocyanine Blue | 5 parts by weight |
| Compound obtained in Example 1 | 2 parts by weight |

The above components were mixed in a Henschel mixer, then kneaded in a biaxial heating kneader, and the mixture extruded from the kneader was cooled at a room temperature, roughly crushed in a hammer mill, finely pulverized in a jet mill pulverizer. The pulverized powder was classified in a classifying machine to collect a portion having an average particle size of 9 μm. Thus, a blue toner was obtained. 100 parts by weight of this toner powder was mixed with 0.5 part by weight of hydrophobic silica (Aerosil R974) functioning as a fluidizing agent and 1 part by weight of rutile type titanium oxide having been treated with stearic acid and functioning as an abrasive. This toner mixture was mixed with a carrier (silicone resin-coated spherical ferrite having a particle size of about 70 μm) to obtain a two-component developer containing the toner in an amount of 5% by weight. The electrified amount of this developer measured by Blow-off Method was 30 μc/g.

Copies were made using the above prepared developer by a commercially available electrophotographic copier under the environmental conditions of 10° C. and 20 RH, 23° C. and 50 RH, and 30° C. and 85 RH. Under any of these conditions, there were obtained clear, blue copies with no fog and no offset. Even after continuously making 50,000 copies under the environmental conditions of 10° C. and 20 RH, and 23° C. and 50 RH, the quality of the copies was not lowered. Furthermore, 10,000 copies were continuously made under the environmental conditions of 30° C. and 85 RH, but the quality of the copies was not deteriorated.

COMPARATIVE EXAMPLE 1

A comparative two-component developer was prepared in quite the same manner as in Example 1 except that azo chromium compound (TRH, manufactured by Hodogaya Kagaku K.K.) was used as a charge control agent in place of the compound obtained in Example 1. The electrified amount of this developer measured by Blow-off Method was 30 μc/g. A copy was made using the above prepared comparative developer in the same manner as in Example 1, thus producing a copy of blue tone. After continuously making 5,000 copies, there were obtained blurred copies with foa.

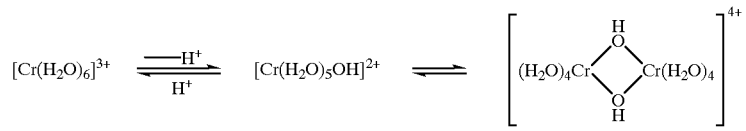

EXAMPLE 3

| Polyester (Runapel 1448, manufactured by Arakawa Kagaku K.K.) | 59.8 parts by weight |
|---|---|
| Magnetic substance (magnetite) | 38.0 parts by weight |
| Wax (polypropylene) | 1.5 parts by weight |
| Compound obtained in Example 1 | 0.7 part by weight |

The above components were mixed in a Henschel mixer, then kneaded in a biaxial heating kneader, and the mixture extruded from the kneader was cooled at a room temperature, roughly crushed in a hammer mill, finely pulverized in a jet mill pulverizer. The pulverized powder was classified in a classifying machine to collect a portion having an average particle size of 9 $\mu$m. Thus, a magnetic toner was obtained. The electrified amount of this toner measured by Blow-off Method was 15 $\mu$c/g. 100 parts by weight of this toner powder was mixed with 0.3 part by weight of hydrophobic silica (Aerosil R972), 0.2 part by weight of silicone resin-coated anatase type titanium oxide and 1 part by weight of calcium carbonate having been treated with a silane coupling agent to obtain a magnetic one-component developer.

Copies were made using the above prepared developer by a commercially available electrophotographic copier under the environmental conditions of 10° C. and 20 RH, 23° C. and 50 RH, and 30° C. and 85 RH. Under any of these conditions, there were obtained clear, black toner images with no fog and no offset. Even after continuously making 150,000 copies under the environmental conditions of 10° C. and 20 RH, 150,000 copies under 30° C. and 85 RH, and 200,000 copies under 23° C. and 50 RH, the quality of the copies (500,000 copies in all) was not lowered to the last copy.

COMPARATIVE EXAMPLE 2

A comparative magnetic one-component developer was prepared in quite the same manner as in Example 3 except that azo chromium compound (S-34, manufactured by Orient K.K.) was used as a charge control agent in place of the compound obtained in Example 1.

Copying was continuously conducted using the above prepared comparative developer in a commercially available electrophotographic copier under the environmental conditions of 30° C. and 85 RH but, when 5,000 copies were made, image density was so lowered that the test was discontinued.

EXAMPLE 4

25 g of NaOH was added to 900 g of water, and the mixture was heated under stirring to completely dissolve NaOH. To this NaOH aqueous solution was added 112.8 g of 3-hydroxy-2-naphthoic acid under stirring to dissolve 3-hydroxy-2-naphthoic acid. When pH of the dissolved solution became 6.9, heating and stirring were discontinued, and the solution was filtered to remove insolubles to prepare a reaction solution A. Separately, 119 g of a 40% CrCl$_3$ solution was added to 500 g of water and stirred to prepare a chromium(III) chloride solution. To this solution was gradually dropwise added 380 g of a 1% NaOH aqueous solution in 2.5 hours to obtain a solution having a pH of 5 to 5.5. This solution was referred to as reaction solution B.

Then, reaction solution B was dropwise added to reaction solution A slowly in about 2 hours. After completion of the dropwise addition, the reaction solution was heated to 70 to 75° C., then cooled to 50° C. and the reaction solution was suction filtered and washed with water to obtain a reaction product. The pH of the filtrate was 4.5. The reaction product collected by filtration was dried at 80° C. to obtain 150 g of an end product.

EXAMPLE 5

A magnetic one-component developer was prepared in quite the same manner as in Example 3 except that the compound obtained in Example 4 was used as a charge control agent in place of the compound obtained in Example 1.

Copies were made using the above prepared developer by a commercially available electrophotographic copier under the environmental conditions of 10° C. and 20 RH, 23° C. and 50 RH, and 30° C. and 85 RH. Under any of these conditions, there were obtained distinct, black toner images with no fog and no offset. Even after continuously making 150,000 copies under the environmental conditions of 10° C. and 20 RH, 150,000 copies under 30° C. and 85 RH, and 50,000 copies under 23° C. and 50 RH, the quality of the copies (350,000 copies in all) was not lowered.

EXAMPLE 6

| Polyester (Runapel 1448, manufactured by Arakawa Kagaku K.K.) | 48.9 parts by weight |
|---|---|
| Magnetic substance (magnetite) | 45.0 parts by weight |
| Wax (polypropylene) | 1.6 parts by weight |
| Compound obtained in Example 1 | 0.5 part by weight |
| CCR (FCA-101, manufactured by Fujikura Kasei K.K.) | 4.0 parts by weight |

The above components were mixed in a Henschel mixer, then kneaded in a biaxial heating kneader, and the mixture extruded from the kneader was cooled at a room temperature, roughly crushed in a hammer mill, finely pulverized in a jet mill pulverizer. The pulverized powder was classified in a classifying machine to collect a portion having an average particle size of 9 $\mu$m. Thus, a magnetic toner was obtained. The electrified amount of this toner measured by Blow-off Method was 15 $\mu$c/g. 100 parts by weight of this toner powder was mixed with 0.4 part by weight of hydrophobic silica (Aerosil R972), 0.1 part by weight of anatase type titanium oxide having been treated with a silane coupling agent and 1 part by weight of calcium carbonate having been treated with an aminosilane coupling agent to obtain a magnetic one-component developer.

Copies were made using the above prepared developer by a commercially available electrophotographic copier under the environmental conditions of 10° C. and 20 RH, 23° C. and 50 RH, and 30° C. and 85 RH. Under any of these conditions, there were obtained distinct, black toner images with no fog and no offset. Even after continuously making 150,000 copies under the environmental conditions of 10° C. and 20 RH, 150,000 copies under 30° C. and 85 RH, and 50,000 copies under 23° C. and 50 RH, the quality of the copies (350,000 copies in all) was not lowered.

As can be seen from the above Examples, the novel trivalent chromium salt of salicylic acid or salicylic acid derivative, which is obtained by the process of the present invention by reacting chromium(III) halide with an alkali metal salt of salicylic acid or its derivative represented by the general formula 1 under specific conditions, can provide a toner having good storage stability, causing no change in copied image density and no fog even when repeatedly used, and providing good toner images under various environment conditions. The toner has no troubles about fixing properties and offset problem and, as a color toner, can provide distinct color images.

It will be appreciated by those skilled in the art that variations in the invention disclosed herein may be made without departing from the spirit of the invention. The invention is not to be limited by the specific embodiments disclosed herein, but only by the scope of the claims appended hereto.

What is claimed is:

1. A process for producing a trivalent chromium salt of salicylic acid or its derivative, which comprises adding an aqueous solution of an alkali metal salt of salicylic acid or its derivative of 6.5 to less than 7.0 in pH to an aqueous solution of chromium(III) halide of 3.0 to 5.8 in pH.

2. The process for producing a trivalent chromium salt of salicylic acid or its derivative as described in claim 1, wherein said salicylic acid or its derivative is a compound represented by the following general formula 1;

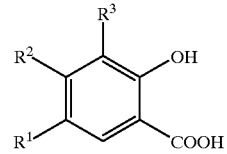

(1)

wherein $R^1$, $R^2$ and $R^3$ each represents a hydrogen atom, a saturated or unsaturated, straight or branched alkyl group or, when taken together, $R^1$ and $R^2$ or $R^2$ and $R^3$ form a fused ring optionally having a saturated or unsaturated, straight or branched alkyl group.

3. The process for producing a trivalent chromium salt of salicylic acid or its derivatives described in claim 2, wherein said salicylic acid derivative represented by the foregoing general formula 1 is 3,5-di-tert-butylsalicylic acid or 3-hydroxy-2-naphthoic acid.

* * * * *